United States Patent
Krivts (Krayvitz) et al.

(10) Patent No.: US 8,772,737 B2
(45) Date of Patent: Jul. 8, 2014

(54) CONDUCTIVE ELEMENT FOR ELECTRICALLY COUPLING AN EUVL MASK TO A SUPPORTING CHUCK

(71) Applicant: Applied Materials Israel, Ltd., Rehovot (IL)

(72) Inventors: Igor Krivts (Krayvitz), Rehovot (IL); Israel Avneri, Ramat-Gan (IL); Yoram Uziel, Misgav (IL); Nir Ben-David Dodzin, Hod Hasharon (IL); Ido Holcman, Rehovot (IL); Itzak Yair, Beer Yaakov (IL); Yosi Basson, Holon (IL)

(73) Assignee: Applied Materials Israel, Ltd., Rehovot (IL)

( * ) Notice: Subject to any disclaimer, the term of this patent is extended or adjusted under 35 U.S.C. 154(b) by 134 days.

(21) Appl. No.: 13/623,804

(22) Filed: Sep. 20, 2012

(65) Prior Publication Data
US 2013/0075605 A1    Mar. 28, 2013

Related U.S. Application Data

(60) Provisional application No. 61/539,971, filed on Sep. 27, 2011.

(51) Int. Cl.
| | |
|---|---|
| *H01J 37/20* | (2006.01) |
| *H01L 21/683* | (2006.01) |
| *G03F 1/14* | (2006.01) |
| *G03F 1/40* | (2012.01) |
| *G03F 1/22* | (2012.01) |

(52) U.S. Cl.
CPC ............ *H01J 37/20* (2013.01); *H01J 2237/20* (2013.01); *H01J 2237/2008* (2013.01); *H01J 2237/0044* (2013.01); *G03F 1/40* (2013.01); *G03F 1/22* (2013.01); *H01L 21/6831* (2013.01)

USPC .................. 250/440.11; 250/307; 250/492.2; 355/75; 378/35; 430/5; 361/234; 257/E21.346; 279/128

(58) Field of Classification Search
CPC .................. H01J 37/20; H01J 2237/20; H01J 2237/2008; H01J 2237/0044; G03F 1/40; G03F 1/22; G03F 7/707; H01L 21/6831; H01L 21/6875
USPC ............ 250/306–311, 440.11, 442.11; 430/5; 361/234; 378/35; 257/E21.346; 279/128; 355/75
See application file for complete search history.

(56) References Cited

U.S. PATENT DOCUMENTS

| | | | | |
|---|---|---|---|---|
| 6,960,772 | B1 * | 11/2005 | Johnson et al. | 250/442.11 |
| 6,984,475 | B1 * | 1/2006 | Levinson et al. | 430/5 |
| 7,514,186 | B2 * | 4/2009 | Meijer et al. | 430/5 |
| 7,952,851 | B2 * | 5/2011 | LaFontaine et al. | 361/234 |
| 2009/0219504 | A1 * | 9/2009 | Hirayanagi | 355/75 |

* cited by examiner

*Primary Examiner* — Jack Berman
(74) *Attorney, Agent, or Firm* — Kilpatrick Townsend & Stockton LLP

(57) ABSTRACT

A coupling module may include an upper portion that defines an aperture, mask contact elements, chuck contact elements and an intermediate element that is connected between the mask contact elements and the upper portion. A shape and a size of the aperture may correspond to a shape and size of a pattern transfer area of an extreme ultra violet (EUVL) mask. The coupling module may be shaped and sized so that once the mask contact elements contact the upper portion of the EUVL mask, the chuck contact elements contact a chuck that supports the mask. The coupling module may further provide at least one conductive path between the upper portion of the EUVL mask and the chuck when the EUVL mask is positioned on the chuck.

15 Claims, 25 Drawing Sheets

Placing on a chuck a EUVL mask and a conductive module. The conductive module can be any of the conductive modules mentioned above. The conductive module electrically couples an upper portion of the EUVL mask and the chuck. 110

Scanning at least a portion of a pattern transfer area of the EUVL mask by a charge particle beam that passes through an aperture that is defined by an upper surface of the conductive module, while the chuck, the conductive module and the charge particle beam are located in a vacuum chamber. 120

CONDUCTIVE ELEMENT FOR ELECTRICALLY COUPLING AN EUVL MASK TO A SUPPORTING CHUCK

RELATED APPLICATIONS

This application is a nonprovisional of and claims priority to U.S. Provisional Application No. 61/539,971, filed Sep. 27, 2011, which is incorporated herein by reference.

FIELD OF THE INVENTION

The present invention relates to extreme ultra violet lithography (EUVL) mask inspection by electron-beam or ion-beam imaging equipment.

BACKGROUND OF THE INVENTION

EUVL masks will be used in next generation lithography processes for making nanometer-scale semiconductor devices. The short EUV wavelength of 13.5 nm enables the creation of smaller devices than possible today with 513 nm lithography.

The lithography process may include exposing silicon wafers coated by photoresist to 13.5 nm wavelength radiation which is reflected from a pattern transfer area of the EUVL mask. The pattern which is located on the top surface of the pattern forming area of the mask is de-magnified and transferred onto the photoresist layer above the silicon wafer. After such an exposure, the lithography process continues. The developed photoresist is removed and a pattern is formed on the silicon by etch or deposition. The EUVL mask also includes a periphery area that may surround the pattern transfer area.

FIG. 1 illustrates an EUVL mask that is built from a non-conductive layer 12 (such as a glass layer) and an upper portion that may include a combination of (a) reflecting layers 14 which reflect the EUV light towards the substrate and (b) an absorbing layer 16. This upper portion is conductive and extends throughout the mask and especially throughout the pattern transfer area of the mask.

FIG. 1 also includes arrows 8 that represent EUVL radiation directed onto the mask and reflected from the mask.

The EUVL mask is positioned on a chuck 50. The chuck 50 may be electrically coupled (by cable 59) to a predetermined location of a known potential (such as the ground).

The EUVL mask must be inspected during its manufacturing and utilization processes. A defect on the top of the mask or a defect buried in the multi-layer stack (on areas which are not covered by the absorber), will cause repetitive defects on the exposed silicon wafers.

SUMMARY OF THE INVENTION

There may be provided a coupling module for coupling an extreme ultra violet (EUVL) mask to a chuck, the coupling module may comprise: an upper portion that defines an aperture; at least one mask contact element; chuck contact elements; and an intermediate element that may be connected between the mask contact elements and the upper portion. The shape and size of the aperture may correspond to a shape and size of a pattern transfer area of the EUVL mask. The coupling module may be shaped and sized so that once the at least one mask contact element contacts an upper portion of the EUVL mask, the chuck contact elements contact a chuck that supports the EUVL mask. The coupling module provides at least one conductive path between the upper portion of the EUVL mask and the chuck, when the EUVL mask may be positioned on the chuck in alignment with the coupling module.

When the EUVL mask may be positioned on the chuck, the coupling module may mask edges of the EUVL mask.

The at least one mask contact element may comprise a spring.

The height difference between the upper portion and a bottom end of the intermediate element may be smaller than a height of the EUVL mask.

The mask contact elements are positioned so as to contact the EUVL mask at locations that are outside the pattern transfer area.

The aperture exposes the pattern transfer area once the coupling module may be placed on the EUVL mask.

The intermediate element may be shaped so as to surround the EUVL mask.

The intermediate element may be shaped so as to contact at least one sidewall of the EUVL mask, when the coupling module is placed on the EUVL mask.

The coupling module may be symmetrical about a center of the EUVL mask.

The coupling module may be made of stainless steel. Alternatively, conductive elements of the coupling module can be made of stainless steel.

The at least one conductive path may be formed by a conductive coating of a non-conductive coupling module.

The at least one conductive path may comprise multiple conductive paths.

At least one mask contact element may be arranged to loosely contact the chuck when the coupling module is placed on the EUVL mask.

The coupling module comprises multiple coupling module conductive portions that are isolated from each other, wherein different coupling module conductive portions are coupled to different mask contact elements, wherein each mask contact element electrically couples a coupling module conductive portion to the EUVL mask.

A method may be provided for inspecting an extreme ultra violet (EUVL) mask. The method may include placing on a chuck an EUVL mask and a coupling module, wherein the coupling module electrically couples an upper portion of the EUVL mask and the chuck, and scanning at least a portion of a pattern transfer area of the EUVL mask by a charged particle beam that passes through an aperture that is defined by an upper portion of the coupling module, while the chuck, the coupling module and the charged particle beam are located in a vacuum chamber.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIG. 18 is a flow chart of a method according to an embodiment of the invention;

DETAILED DESCRIPTION OF THE DRAWINGS

Figure 1:
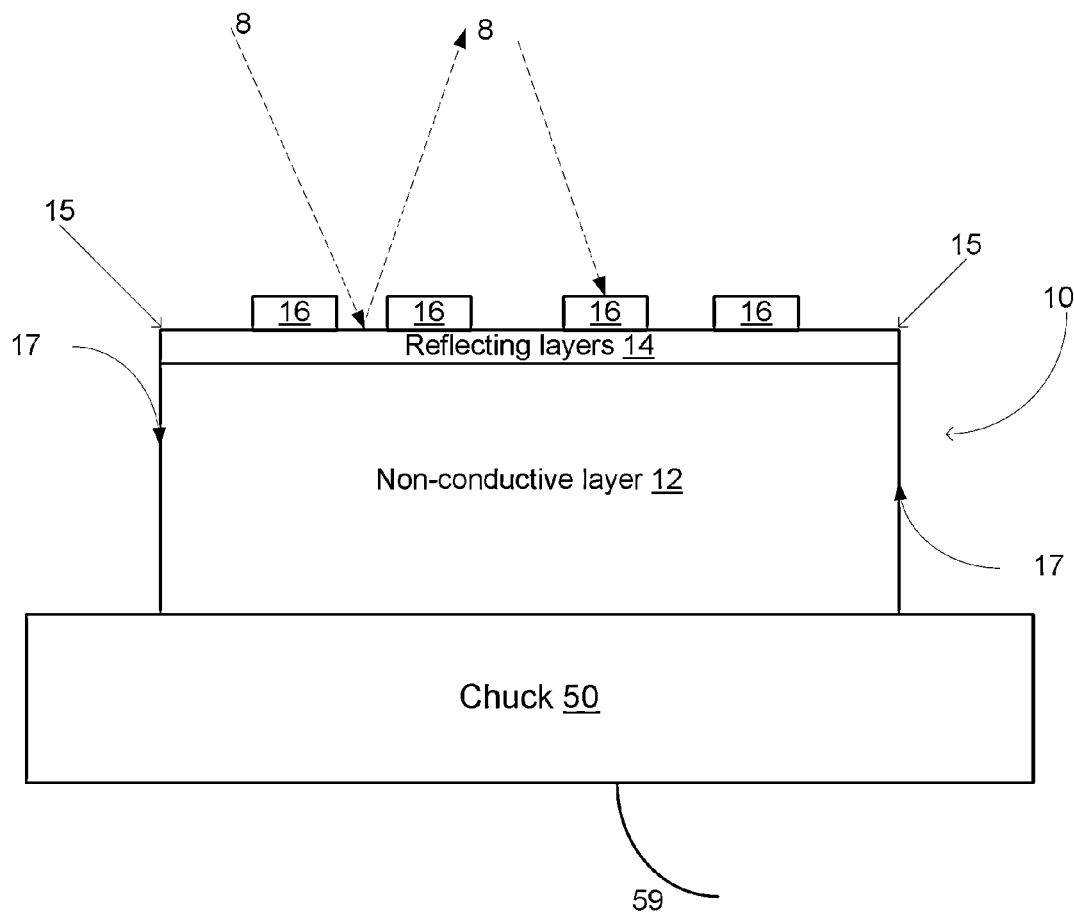
FIG. 1 is a side view of a prior art EUVL mask and chuck.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Various figures illustrate the upper portion of the coupling module as being a flat surface. It is noted that the upper portion can be an upper surface or have any other shape.

A coupling module is a module that has conductive parts that are expected to be a part of conductive paths between an EUVL mask and a chuck, when the EUVL mask is positioned on the chuck and is in alignment with the coupling module. The conductive module can be a conductive frame but may have other forms or shapes.

The upper portion (top layer—including layers 16 and 14) of the EUVL mask 10 can be inspected with different imaging technologies that may include EUVL mask inspection by electron beams (e-beams) or ion beam imaging. Inspection by e-beam or ion beam is performed inside vacuum chambers.

An EUVL mask 10 is inserted into a vacuum chamber (not shown) and is positioned on a chuck 50 which may be located on top of a stage such as but not limited to an XY stage. During inspection, the EUVL mask 10 is translated (moved in the X and/or Y directions) under the electron or ion beam.

As mentioned above, the upper portion of the EUVL mask 10 is made of conductive layers (14 and 16) that are located on top of a non-conductive layer 12. The latter may be relatively thick (about 6 mm) and may be made of a quartz plate.

Scanning the EUVL mask 10 with a charged particle beam may cause a buildup of electrical charge. In order to eliminate buildup of electric charge (which can cause damage) during the inspection of the EUVL mask, the upper portion of the EUVL mask should be electrically coupled to the chuck 50—as the chuck 50 is conductive. The chuck 50 (and especially the chuck base) may be connected to the required electric potential. For example, the chuck 50 may be grounded.

There may be provided a coupling module that enables an electric connection of the upper portion of the EUVL mask to the chuck during inspection as follows.

A coupling module can be placed above the EUVL mask during the EUVL mask handling process. The coupling module can be open from above (it may define an aperture that exposes the pattern transfer area 11 of the EUVL mask 10), but touches the EUVL mask 10 in various (for example—2, 3, 4 or more) points that may be located outside the pattern transfer area, such as in a peripheral area of the EUVL mask.

The coupling module may be translated as part of the EUVL mask assembly onto the inspection tool. A robot (or other transfer unit) can carry the EUVL mask and the coupling module (either together or separately), can position the EUVL mask within a vacuum chamber, can place the EUVL on the chuck, and can place the coupling module on the EUVL mask and the chuck.

The coupling module can be made of conductive materials, may include conductive and isolating materials or may be coated by a conductive coating.

Handling of the EUVL Mask and the Frame

The robotic arm can carry the EUVL mask on its way to the inspection tool.

It is noted that various steps in the loading or unloading of the EUVL mask are known and require no further explanations. These steps may include opening, by a robotic arm, an EUVL mask box (in which the EUVL mask is positioned between inspection and/or lithography processes), extracting the EUVL mask and even (if required) inverting it so that its face is upside down and the like.

The robotic arm can perform self-alignment positioning of the coupling module by virtue of a vertical motion—moving the EUVL mask up into the coupling module.

The coupling module can initially sit atop a base (outside of the vacuum chamber).

The robotic arm can then lift the coupling module by a vertical motion of the arm and the EUVL mask.

The coupling module can self-align to the EUVL mask (for example—by light contact with the side wall of the EUVL mask).

The vertical motion can be performed slowly in order to reduce friction and its generation of molecular contamination.

At the end of the vertical motion, the coupling module is positioned on top the EUVL mask surface, touching various points.

The robotic arm can finally place the EUVL mask with the attached coupling module on the EUVL mask inspection tool chuck.

The chuck can be positioned in a vacuum chamber that may have an opening (which is not shown). This may enable the robotic arm to move within that opening until the EUVL mask contacts the chuck. Then, the EUVL mask moves further down (by the robotic arm) and is extracted.

Figure 8:
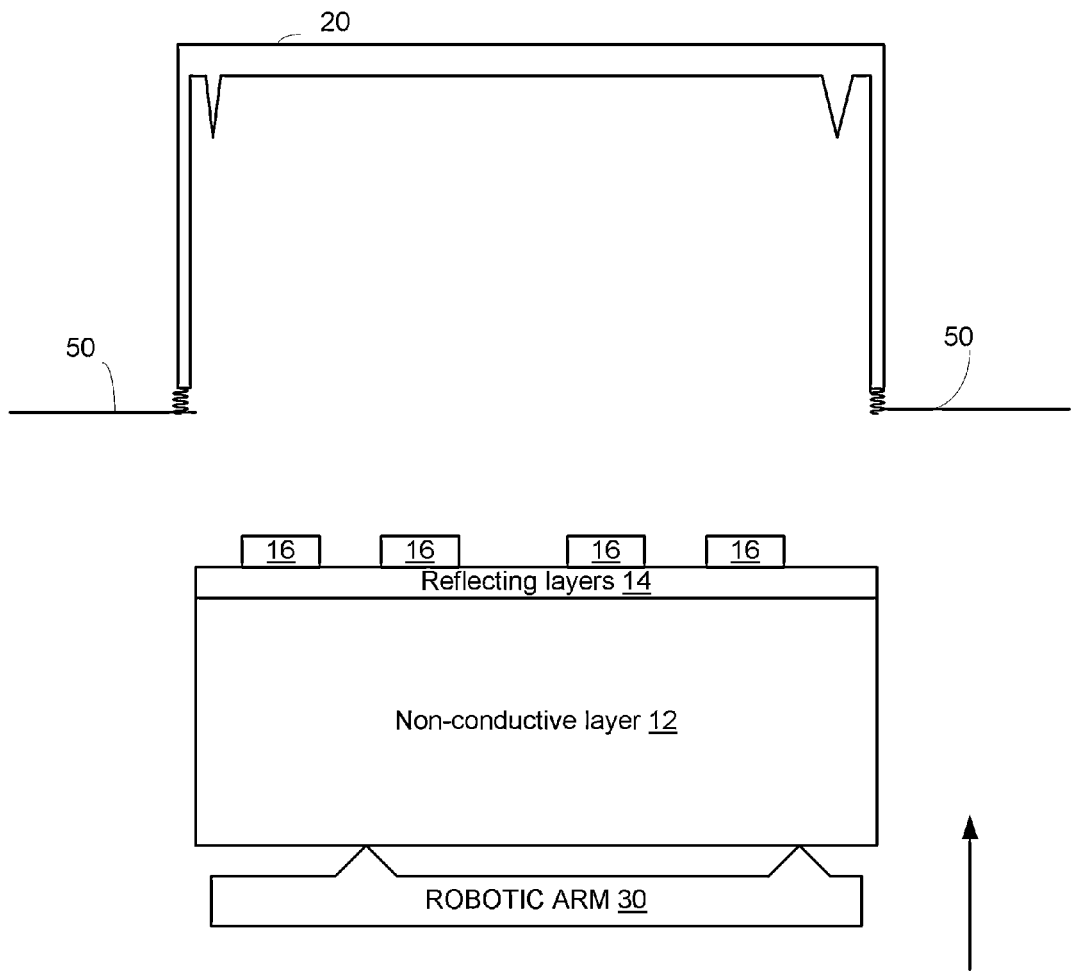
FIGS. 8 and 9 illustrate two stages in a process of placing the coupling module on an EUVL mask and placing the EUVL mask and the coupling module on a chuck, according to an embodiment of the invention.
Figure 9:
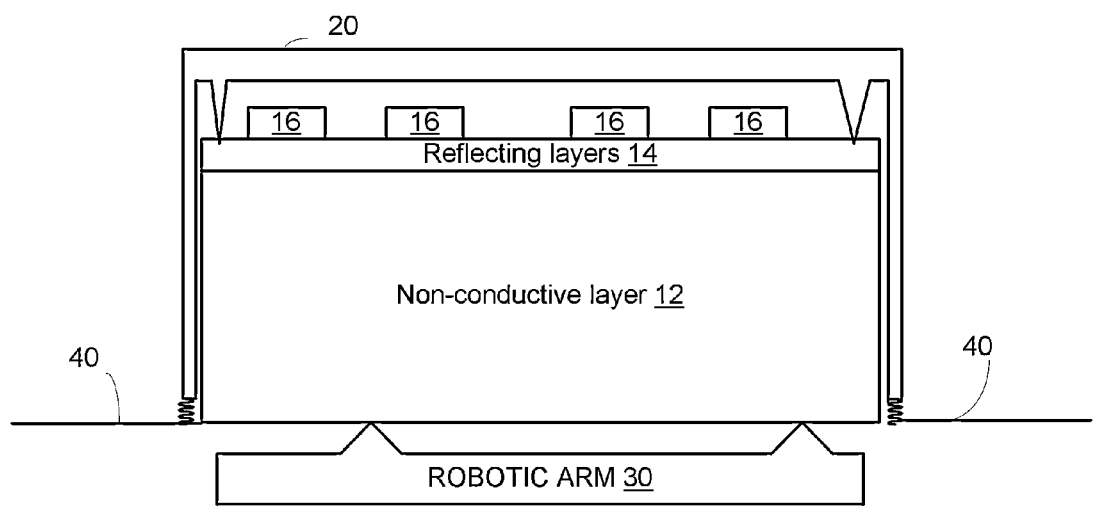

The loading process is illustrated in FIGS. 8 and 9.

When the inspection job has completed, the robotic arm returns and lifts the EUVL mask and the coupling module.

The coupling module can be unloaded from the EUVL mask in series of reversed steps. The coupling module can be left on its base and the robotic arm continues with returning the EUVL mask into its box.

The coupling module can be portable and can be loaded on the EUVL mask by a standard EUVL mask handling robotic arm.

The Coupling Module and the EUVL Mask

According to an embodiment of the invention, the coupling module contacts the chuck in a loose manner—it can be connected via springs (or other elastic elements) that are attached to the coupling module. The springs contract slightly, which enables the electric contact to occur, but prevents the coupling module from being lifted by the spring force and hence to lose its contact with the EUVL mask surface.

A spring can be located in proximity to the EUVL mask (and even contact it) or can be slightly spaced apart from the EUVL mask (and even remotely placed from the EUVL mask). If the latter occurs (remote position), then the springs can cause potential electrical arcing (if any) to be formed far removed from the EUVL mask itself, thereby reducing contamination.

The coupling module can be made of nonconductive material with conductive coating or wiring, to enable the creation of contacts only between specific points on the coupling module. Such feature enables the monitoring of the quality of contact between the coupling module legs and the EUVL mask's top surface.

According to an embodiment of the invention, a coupling module may be provided and may include an upper portion that defines an aperture, mask contact elements, chuck contact elements and an intermediate element that may be connected between the mask contact elements and the upper portion. A shape and a size of the aperture correspond to a shape and size of a pattern transfer area of an extreme ultra violet (EUVL) mask. The coupling module may be shaped and sized so that once the mask contact elements contact the upper portion of the EUVL mask, the mask chuck contact elements contact a chuck that supports the mask. The coupling module may provide at least one conductive path between the upper portion of the EUVL mask and a chuck, when the EUVL mask may be positioned on the chuck.

FIGS. 2-6 illustrate various elements (12, 14 and 16) of EUVL mask 10, chuck 50 and coupling module 20. The coupling module 20 electrically couples the upper portion (especially layers 14 and additionally or alternatively layers 16) to the chuck 50.

FIGS. 2-6 illustrate the aperture 22 formed at the upper portion 21 of the coupling module 20. The edges of the aperture 22 are illustrated in this cross sectional view by two spaced-apart dashed lines 25.

Figure 2:
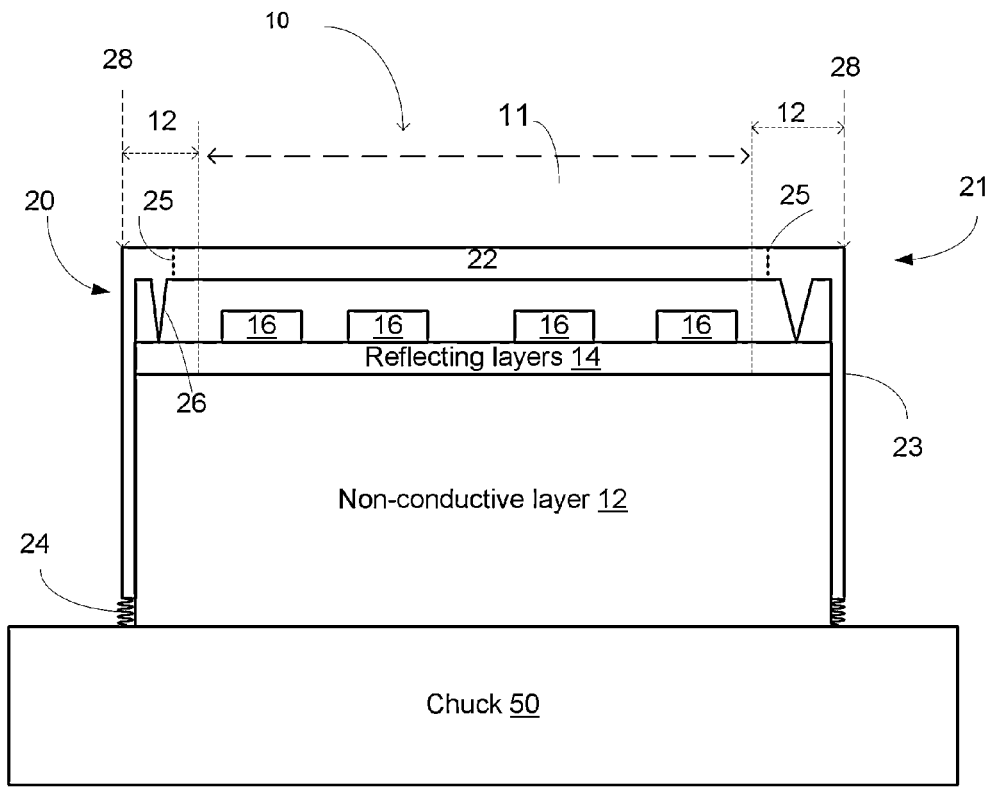
FIG. 2 illustrates a chuck, an EUVL mask and a coupling module, according to an embodiment of the invention.
Figure 5:
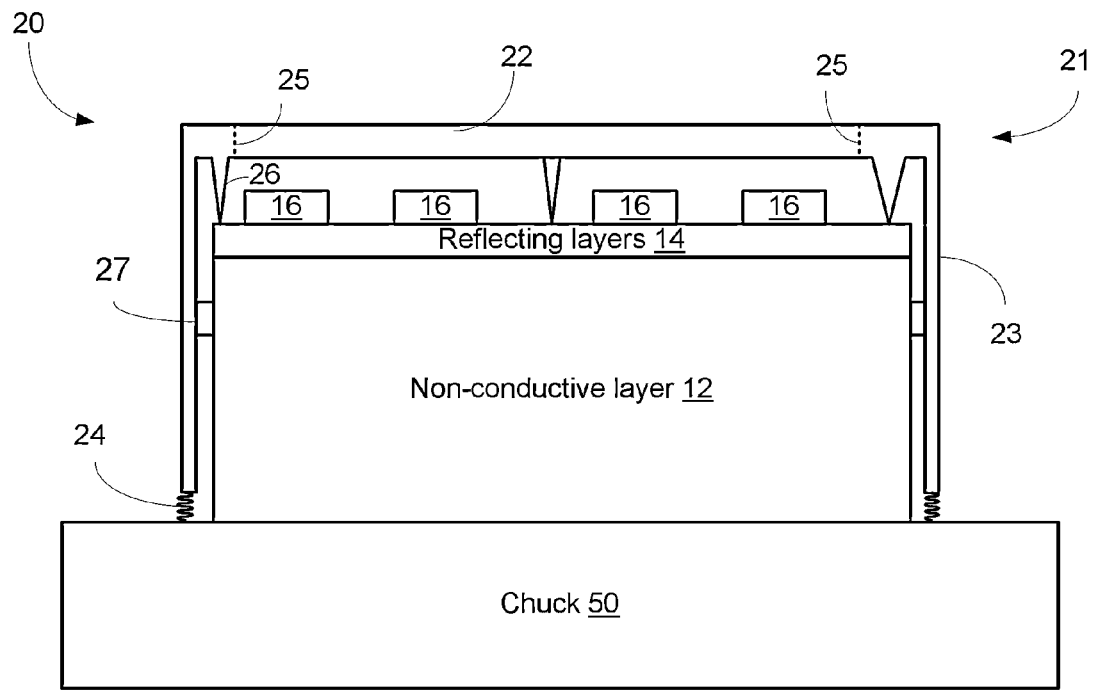
FIG. 5 illustrates a chuck, an EUVL mask and a coupling module, according to a further embodiment of the invention.
Figure 6:
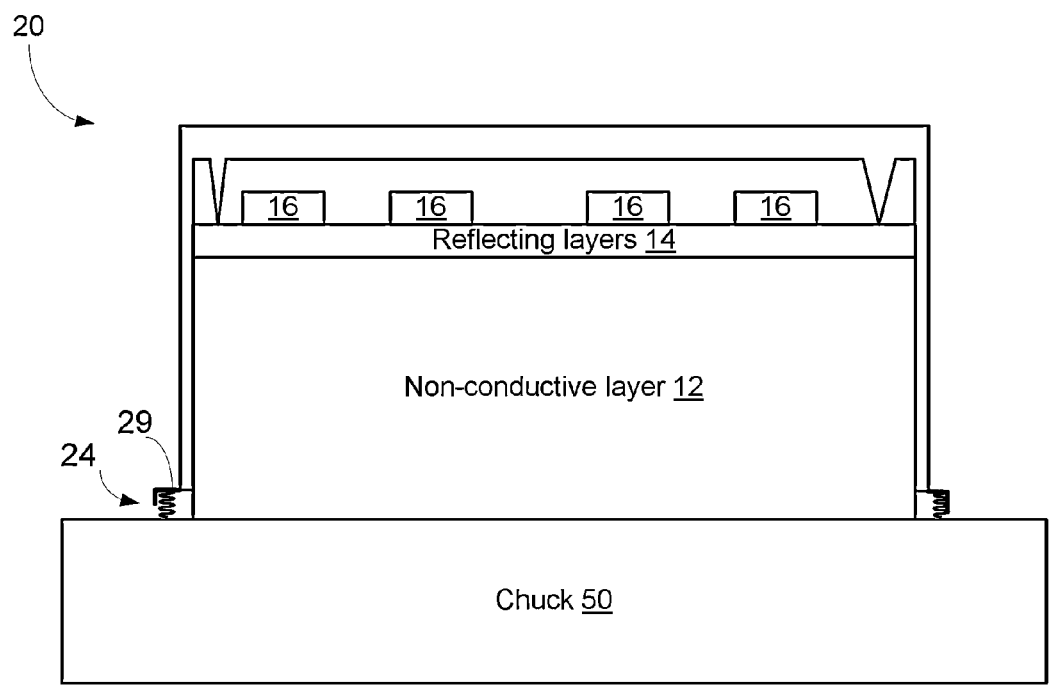
FIG. 6 illustrates a chuck, an EUVL mask and a coupling module, according to a yet further embodiment of the invention.

FIGS. 2, 5 and 6 illustrate mask contact element that include springs 24. The springs 24 may be included in housing 29 or connected to the intermediate element 23 in various other manners.

FIGS. 2 and 5 illustrate the springs 24 as being located below the intermediate element 23 and very proximate to the external sidewalls 17 of the EUVL mask 10 while FIG. 6 illustrates springs 24 as being more distant from the EUVL mask 10 than the intermediate element 23. FIG. 5 illustrates spacers 27 between the external sidewalls 17 of the EUVL mask 10 and the walls of the intermediate element 23.

FIG. 6 shows a combination of housings 29 that partially surround springs 24 that loosely contact the chuck 50.

Figure 3:
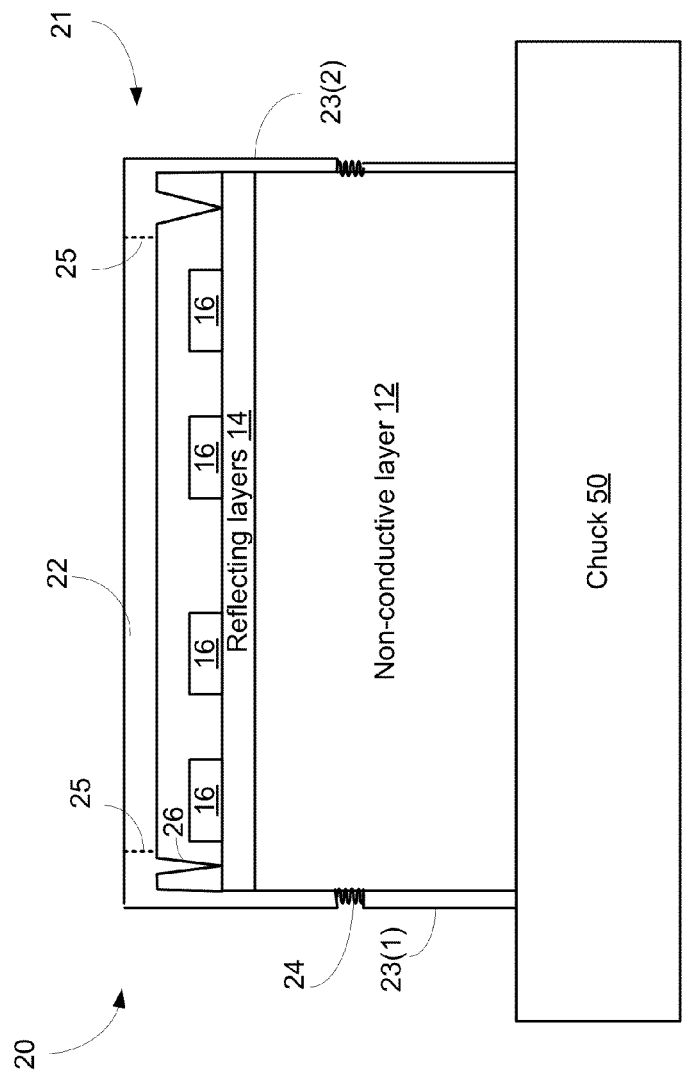
FIG. 3 illustrates a chuck, an EUVL mask and a coupling module, according to another embodiment of the invention.

FIG. 3 illustrates springs 24 as being connected between two parts 23(1) and 23(2) of the intermediate element 23 so that the lower part 23(1) of the intermediate element 23 (and not the springs 24) touch the chuck 50.

Figure 13:
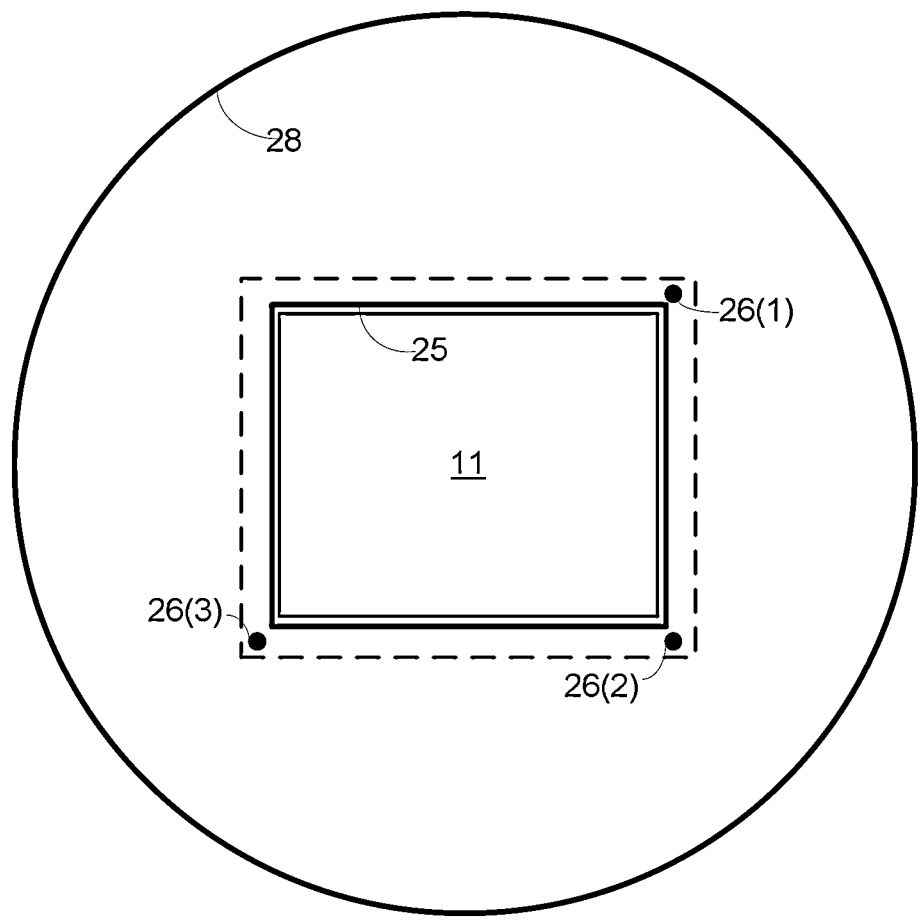
FIG. 13 illustrates an EUVL mask and a coupling module, according to an embodiment of the invention.
Figure 14:
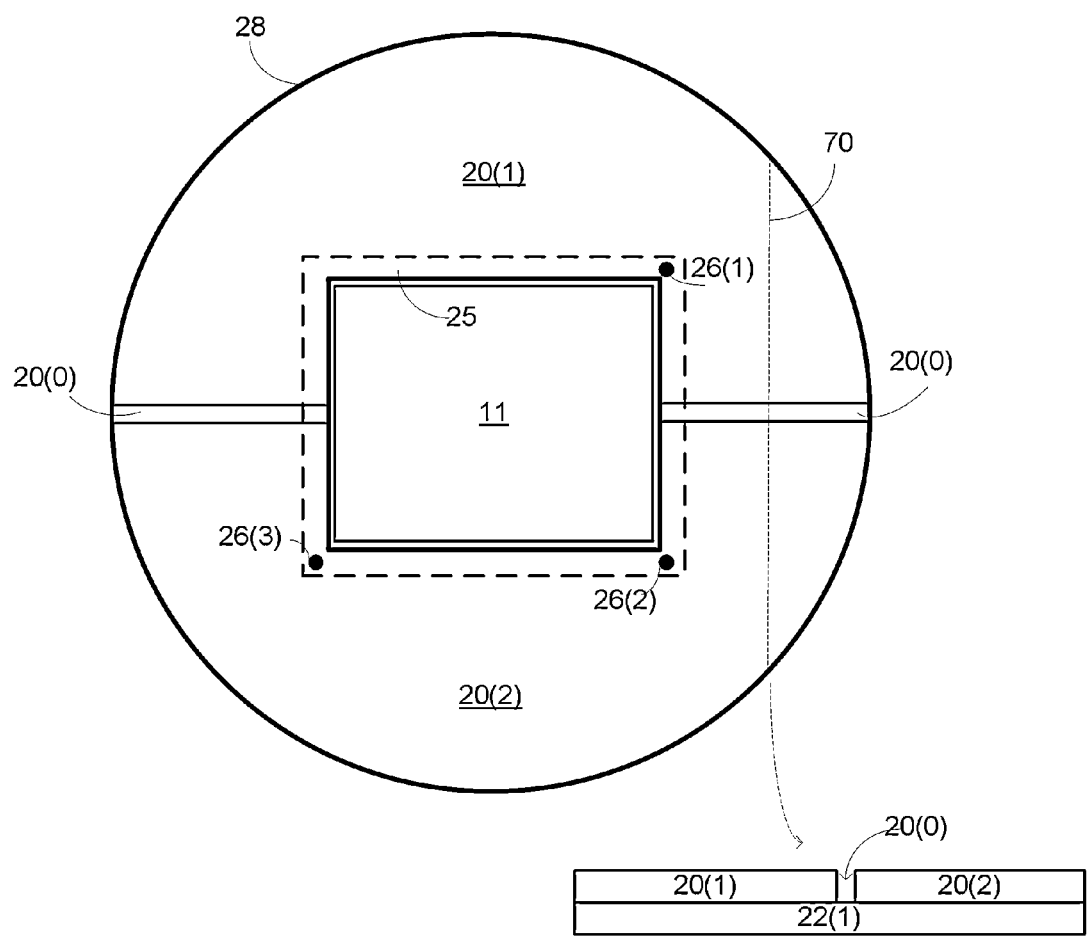
FIG. 14 includes a top view of an EUVL mask and a coupling module and also includes a cross sectional view of the coupling module, according to an embodiment of the invention.
Figure 15:
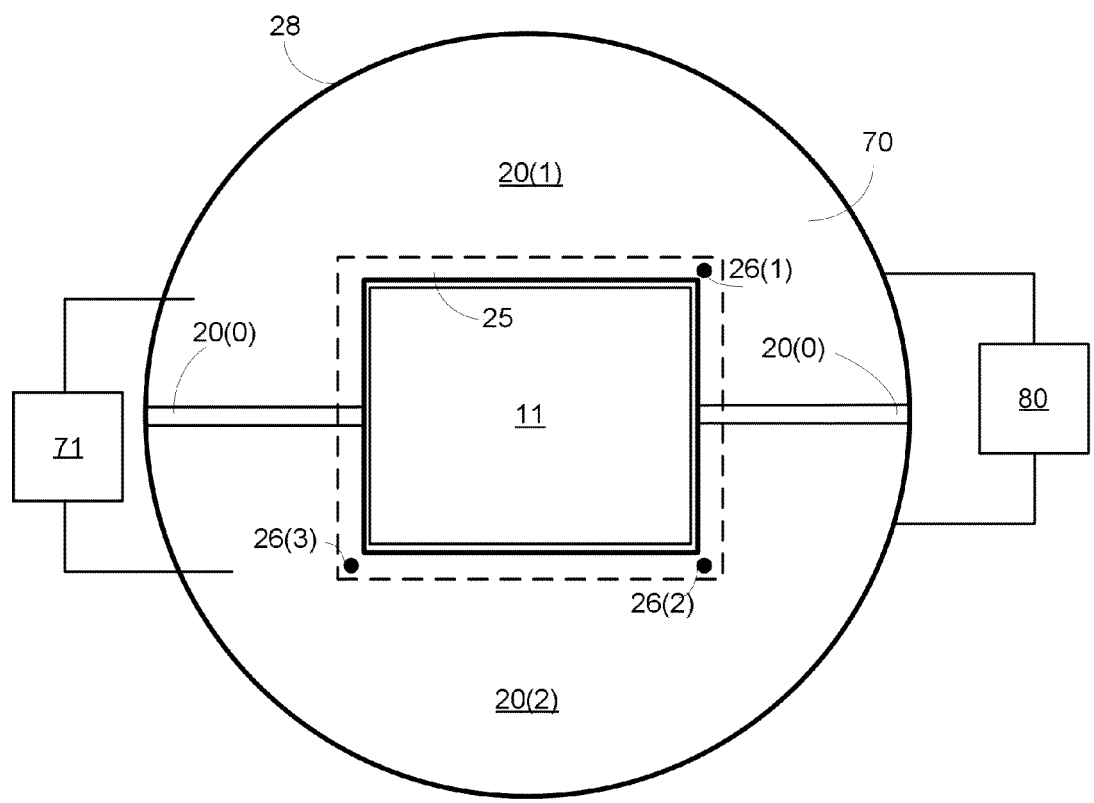
FIG. 15 is a top view of an EUVL mask, a measurement device, a voltage supplier and a coupling module, according to an embodiment of the invention.

FIGS. 2-4 and 6 illustrate two spike shaped mask contact elements 26 while FIG. 5 illustrates more than two spike shaped mask contact elements 26. FIGS. 13-15 illustrate three mask contacting elements 26(1), 26(2) and 26(3).

Figure 4:
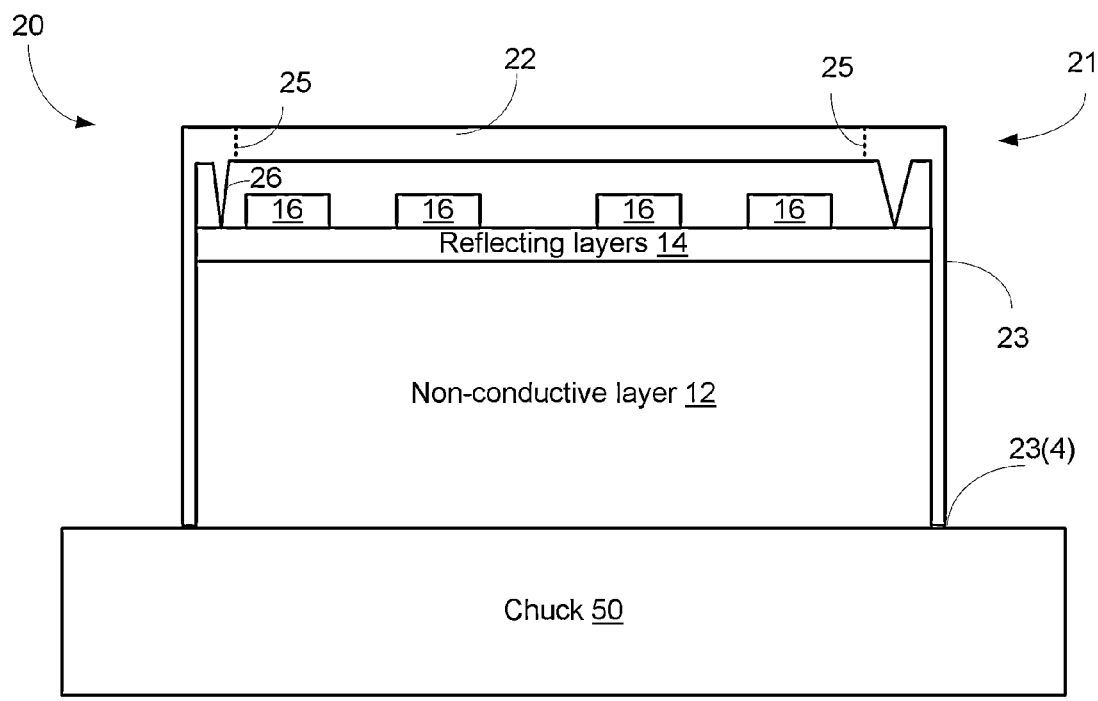
FIG. 4 illustrates a chuck, an EUVL mask and a coupling module, according to yet another embodiment of the invention.

FIG. 4 illustrates an embodiment of the invention in which a height difference between the upper portion 21 and a bottom end 23(4) of the intermediate element 23 may be smaller than a height of the EUVL mask 10.

Figure 7:
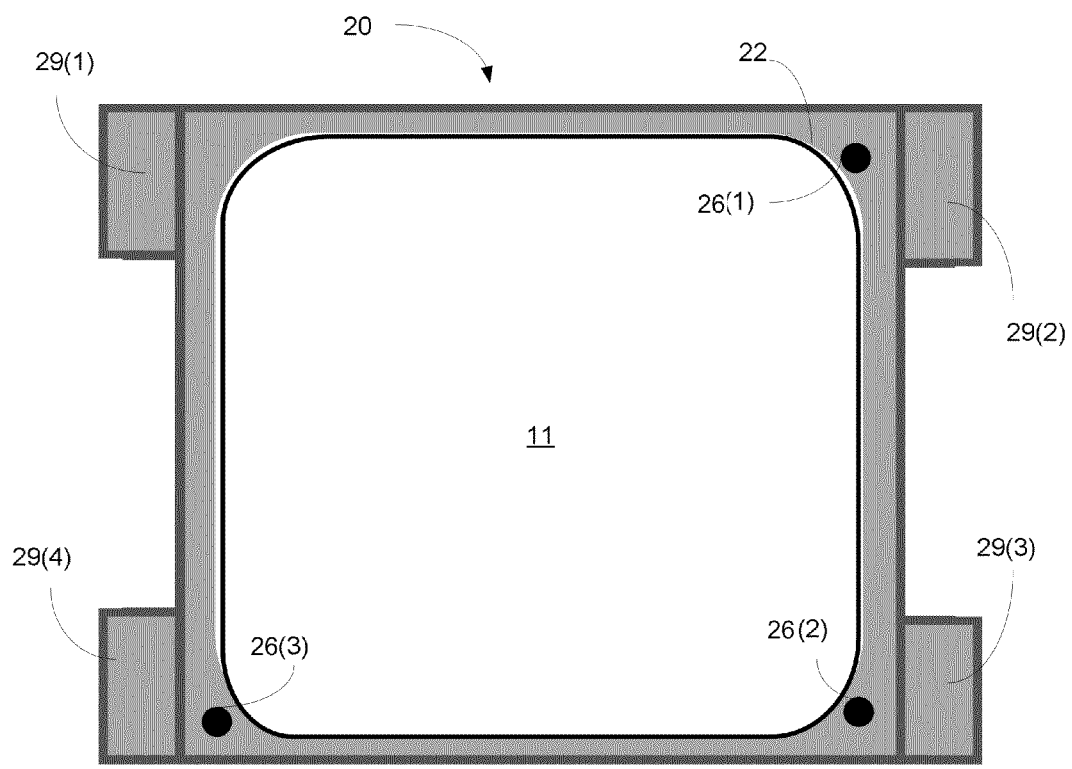
FIG. 7 is a top view of a coupling module, according to a further embodiment of the invention.

FIG. 7 is a top view of coupling module 20 that illustrates aperture 22 being slightly larger than the pattern transfer area 11 of the EUVL mask.

The mask contact elements 26(1)-26(3) are positioned so as to contact the EUVL mask at locations that are not included in the pattern transfer area.

Figure 10:
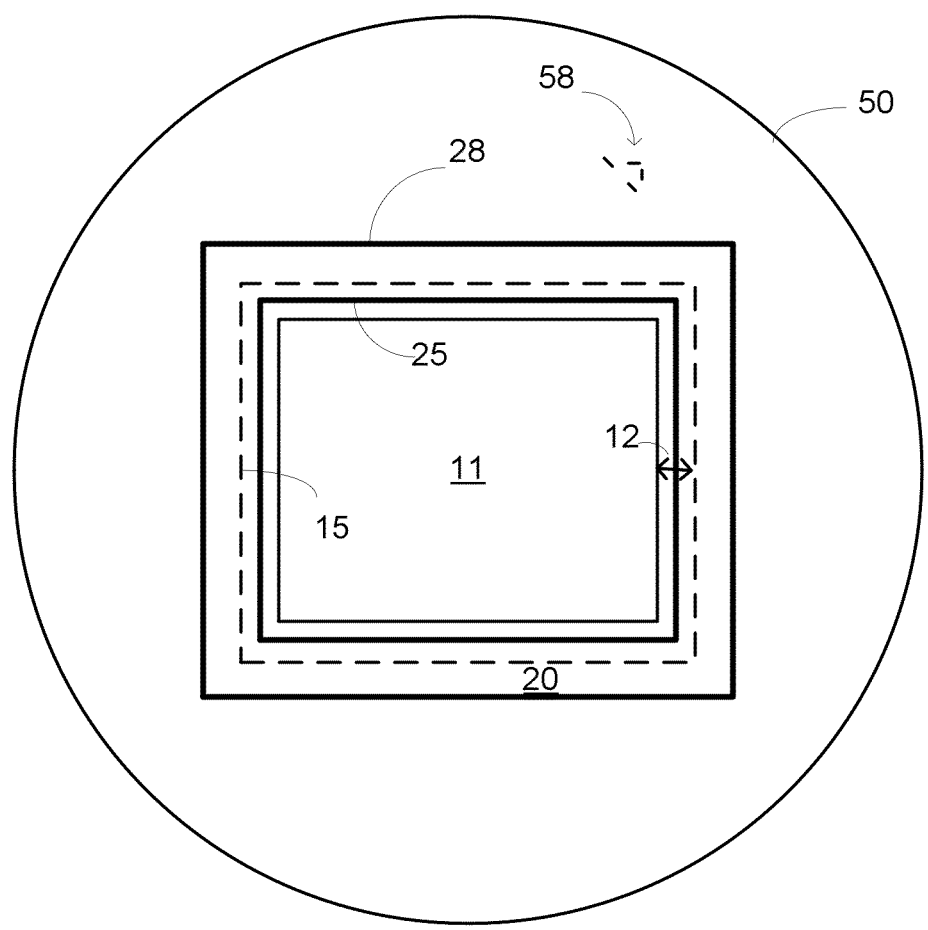
FIGS. 10-12 illustrate a chuck, an EUVL mask and a coupling module, according to an embodiment of the invention.
Figure 11:
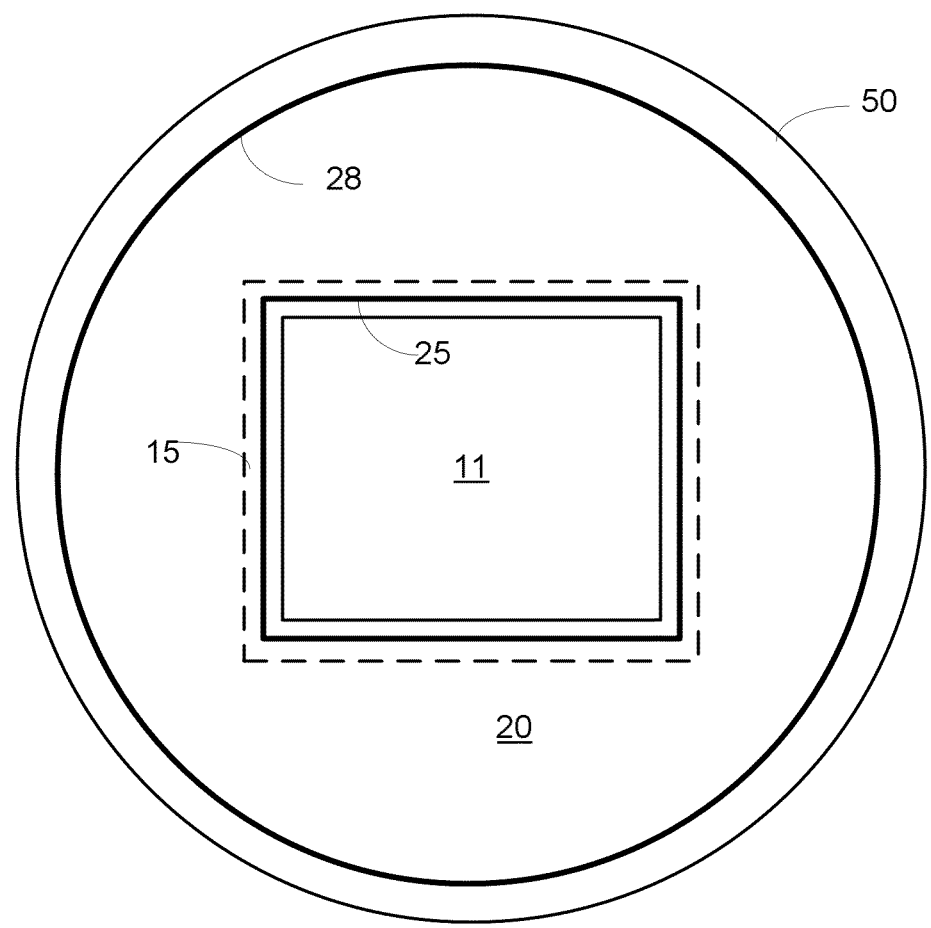
Figure 12:
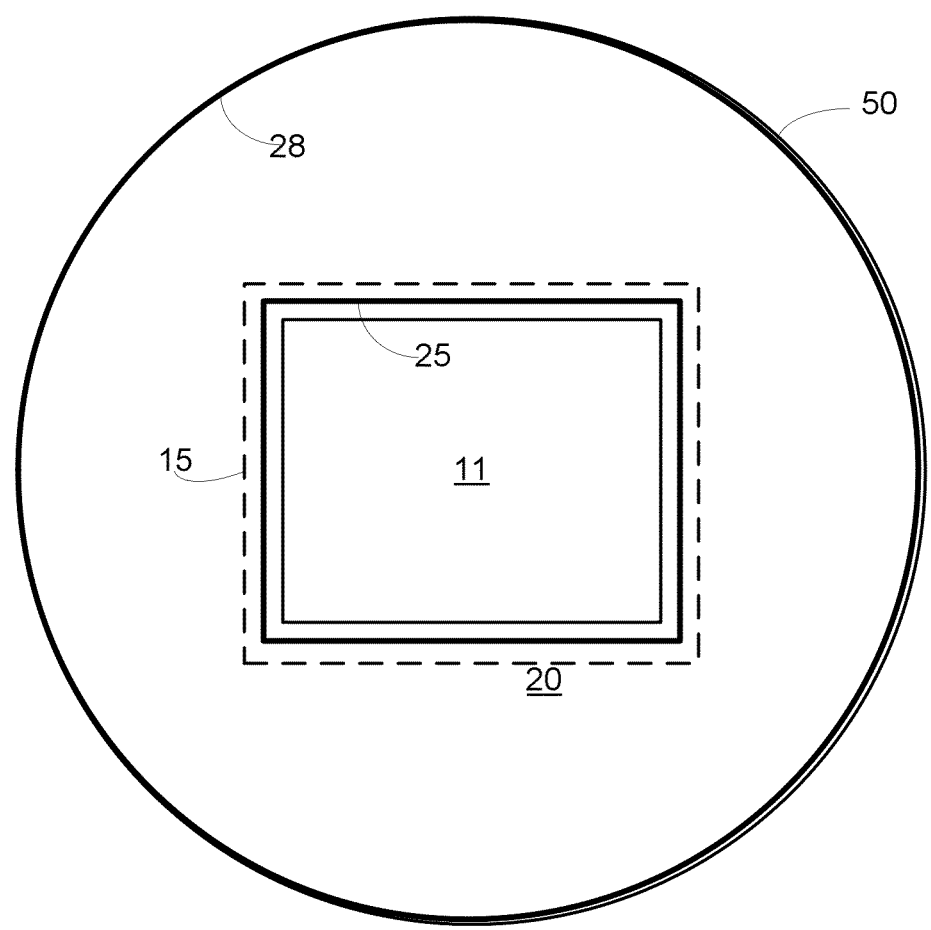

FIGS. 10-12 illustrate a chuck 50, an EUVL mask 10 and a coupling module 20, according to an embodiment of the invention.

Referring to FIG. 10, the chuck 50 has a circular shape and its size should be adapted to the size of the wafer it is expected to support. For example 300 mm wafers (i.e., circular wafers that have a diameter of 300 millimeter) may be supported by circular chucks that may be have a diameter of at least 300 mm.

The EUVL mask 10 is much smaller than the chuck 50 and may have a rectangular shape (although other shapes of chucks and masks may be used). The EUVL mask 10 may include a pattern transfer area 11 that is surrounded by a peripheral area 12 that is not used for transferring patterns onto a wafer.

FIG. 10 illustrates the (internal) edge 25 of the aperture 22 of the coupling module 20, the external edges 15 of the EUVL mask 10, and the external edge 28 of the coupling module 20.

The chuck 50 is usually not perfectly flat. It usually includes various chuck elements (e.g., vacuum apertures, pipes, holding elements, or other spaces or protuberances) that may be located in various locations of the chuck. These various chuck elements are denoted 58 in FIG. 10 and are shown (for convenience of explanation only) as being located at the upper right part of chuck 50.

When the chuck 50 is charged to high voltages (for example, several thousand volts), these chuck elements 58 (as well as edges of the EUVL mask 10) can attribute to the formation of arcs, sparks and the like. According to various embodiments of the invention, the coupling module 20 may cover these element (or at least some of these elements) and reduce the chances of the occurrence of unwanted electrical or electrostatic phenomena.

FIGS. 11-15 illustrate coupling modules 20 that either mask the entire chuck 50 or most of the chuck 50. This masking reduces the irregularities or other chuck elements 58 that may assist in the formation of unwanted electrical or electrostatic phenomena.

In FIG. 11, the coupling module 20 is almost as large as the chuck 50, and has a circular shape.

In FIG. 12, the coupling module 20 has the same size as the chuck 50.

FIG. 13 illustrates an EUVL mask 10 and a coupling module 20, according to an embodiment of the invention.

FIG. 13 illustrates a coupling module 20 that may be as large as the entire chuck 50 and has three mask contact elements—26(1), 26(2) and 26(3).

First mask contact element 26(1) contacts the upper right edge of the peripheral area 12 of the EUVL mask 10. Second mask contact element 26(2) contacts the lower right edge of the peripheral area 12 of the EUVL mask 10. Third mask contact element 26(3) contacts the lower left edge of the peripheral area 12 of the EUVL mask 10. Each of the mask contact elements 26(1)-26(3) provides a conductive path between the coupling module 20 and the mask 10.

Electrical Testing and Breaking Oxidation Layer

FIG. 14 includes (a) a top view of EUVL mask 10 and coupling module 20 and (b) a cross sectional view (taken along imaginary line 70) of the coupling module 20, according to an embodiment of the invention.

FIG. 14 illustrates the coupling module 20 as including two coupling module conductive portions 20(1) and 20(2) that are isolated from each other.

Figure 17:
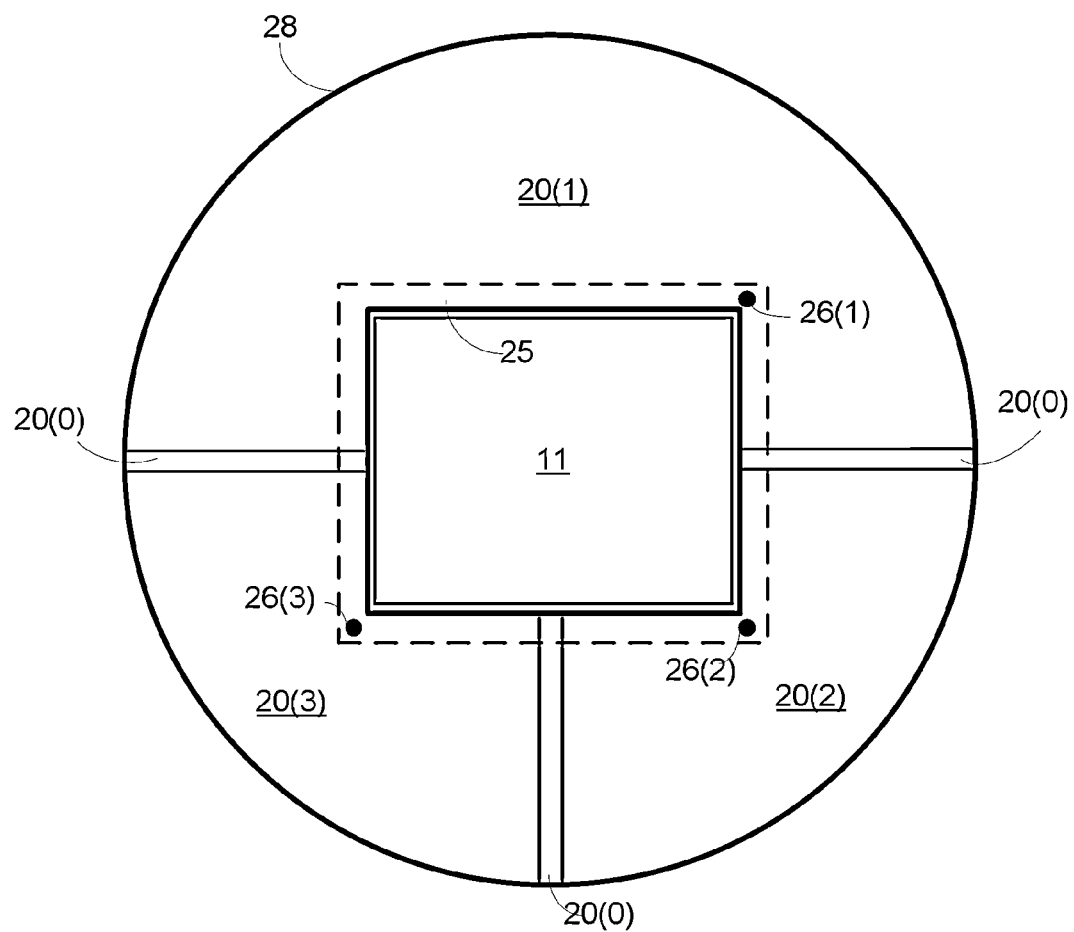
FIG. 17 is a top view of an EUVL mask and a coupling module, according to an embodiment of the invention.

FIG. 17 illustrates the coupling module 20 as including three coupling module conductive portions 20(1), 20(2) and 20(3) that are isolated from each other. Each of these three coupling module conductive portions is electrically coupled to a different mask contact element out of mask contact elements 26(1)-26(3).

The isolation between the different coupling module conductive portions can be achieved by placing an insulating material between these coupling module conductive portions or by forming a gap (such as gap 20(0)) between the coupling module conductive portions. The cross sectional view of FIG. 14 illustrates the upper portion 22 of the coupling module 20 as including a lower layer 22(1) that is made from insulating material. The lower layer 22(1) supports the coupling module conductive portions 20(1) and 20(2) while maintaining a gap 20(0) between the coupling module conductive portions 20(1) and 20(2).

The first coupling module conductive portion 20(1) contacts the first mask contact element 26(1) while the second coupling module conductive portion 20(2) contacts the second and third mask contact elements 26(2) and 26(3).

The first and second coupling module conductive portions 20(1) and 20(2) can be shorted to each other by the EUVL mask 10—via the first, second and third mask contact elements 26(1), 26(2) and 26(3).

In other words, if the first through third mask contact elements 26(1)-26(3) are electrically coupled to the EUVL mask 10, then they can form a part of a conductive path between the first and second coupling module conductive portions 20(1) and 20(2).

If, for example, the first mask contact element 26(1) does not contact the EUVL mask 10, or for any other reason is not electrically coupled to the EUVL mask 10, then the first and second coupling module conductive portions 20(1) and 20(2) may remain isolated from each other.

Accordingly, an evaluation of the coupling between the first and second coupling module conductive portions 20(1) and 20(2) can indicate whether the first through third mask contact elements 26(1)-26(3) properly contact the EUVL mask 10. Thus, the first and second coupling module conductive portions 20(1) and 20(2) can be electrically coupled to different terminals of a measurement device (such as measurement device 71 of FIG. 15) such as an ohmmeter, voltmeter, amperemeter and the like.

Figure 16:
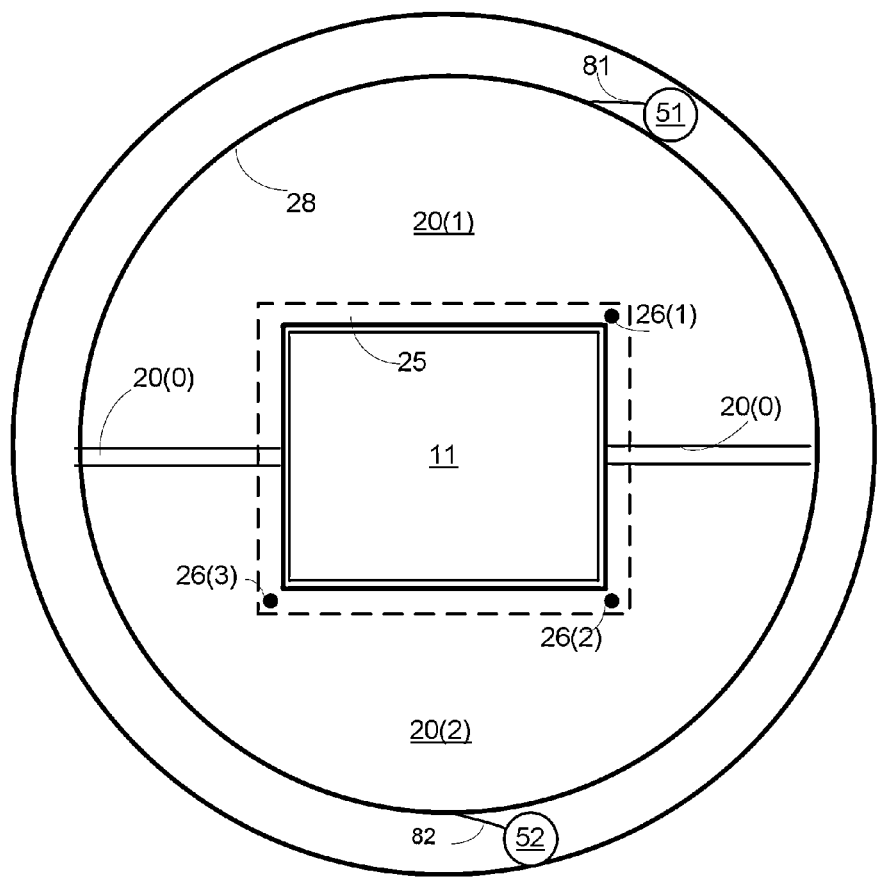
FIG. 16 is a top view of an EUVL mask, a chuck and a coupling module, according to an embodiment of the invention.

It is noted that such measurements may be based upon the assumption that the first and second coupling module conductive portions 20(1) and 20(2) are not shorted by the chuck 50—and this can be achieved by coupling them to electrically isolated elements of the chuck 50. FIG. 16 illustrates two mutually isolated elements 51 and 52 of chuck 50 that are electrically coupled (via conductors 81 and 82 respectively) to the first and second coupling module conductive portions 20(1) and 20(2).

The conductive parts of the EUVL mask 10 can be oxidated so that an unwanted oxidation layer may be formed at the upper portion of the EUVL mask 10. This oxidation layer is not conductive and it may prevent the formation of a conductive path between the mask contact elements 26(1)-26(3) when the latter contact the EUVL mask 10.

This prevents the first and second coupling module conductive portions 20(1) and 20(2) from being electrically coupled to each other via the EUVL mask 10.

While measurement device 71 can detect such problems, voltage supply 0 can assist in resolving this problem—by generating voltage pulses (or other electrical signal) that may be high enough to remove the oxidation layer—or at least removing the oxidation layers at locations that are contacted by the mask contact elements 26(1)-26(3).

Measurement device 70 and voltage supply 80 can participate in a process that includes one or more iterations of (a) evaluating if the first and second coupling module conductive portions 20(1) and 20(2) are electrically coupled to each other (may be equivalent to a determination of whether an oxidation layer exists); and (b) applying a voltage signal by the voltage supplier 80 to break the oxidation layer—if it is determined that such an oxidation layer exists.

If one iteration fails then the next iteration can be preceded by changing the signal (for example—increasing the voltage) to be supplied during the next iteration. Non-limiting values may range between a few volts to a few hundred volts, for example, between 3V and 400V.

FIG. 18 illustrates method 100 according to an embodiment of the invention.

Method 100 may be applied for inspecting an extreme ultra violet (EUVL) mask.

Method 100 may start by stage 110 of placing on a chuck an EUVL mask and a coupling module. The coupling module can be any of the coupling modules mentioned above. The coupling module electrically couples an upper portion of the EUVL mask and the chuck.

Stage 110 may be followed by stage 120 of scanning at least a portion of a pattern transfer area of the EUVL mask by a charged particle beam that passes through an aperture that is defined by an upper portion of the coupling module, while the chuck, the coupling module and the charged particle beam are located in a vacuum chamber.

The coupling module can be any of the mentioned above coupling modules. The method can include any stages of loading and, additionally unloading the coupling module and the EUVL mask from the vacuum chamber.

For simplicity of explanation, FIG. 18 does not show the stages of placing the EUVL mask and the coupling module in the vacuum chamber and removing the coupling module and the mask from the vacuum chamber.

Figure 19:
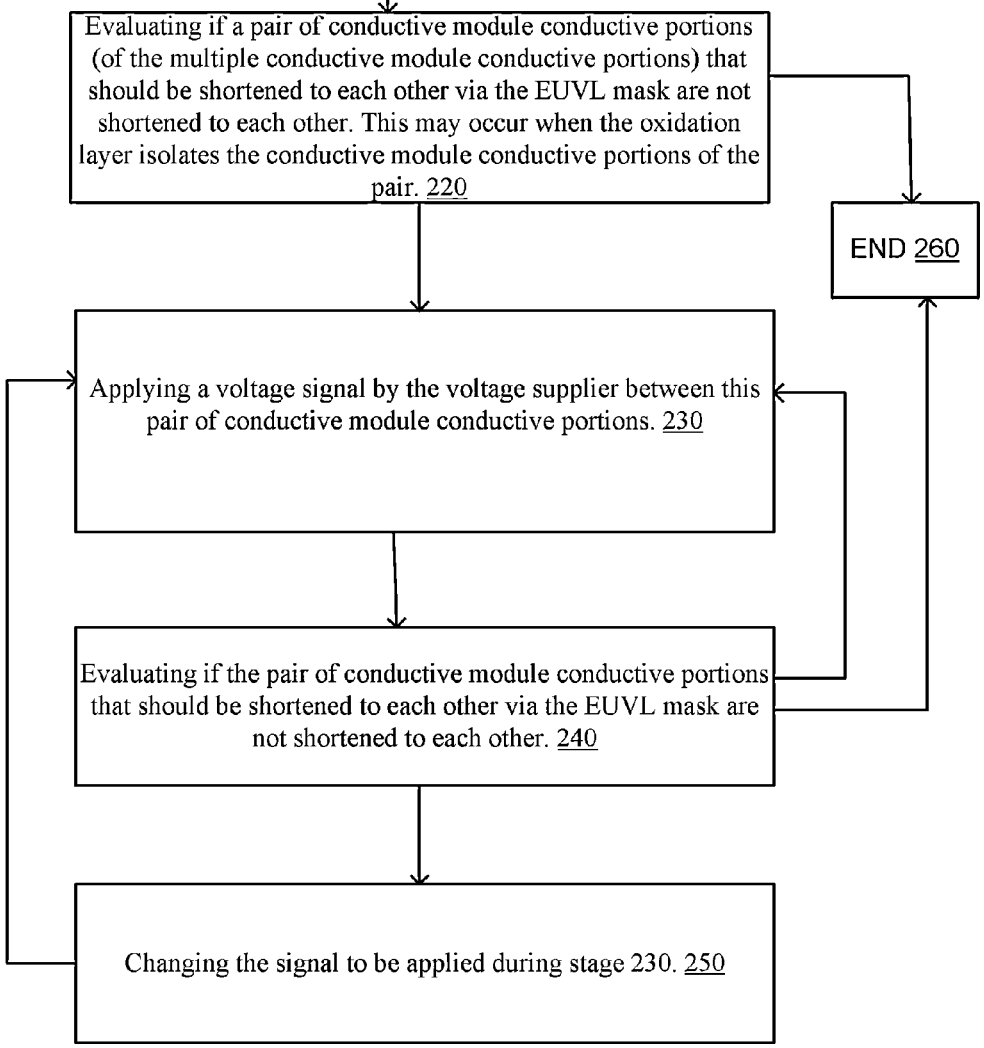
FIG. 19 is a flow chart of a method according to an embodiment of the invention.

FIG. 19 illustrates method 200 for improving a conductivity of an electrical path formed between mask contact elements and an EUVL mask, according to an embodiment of the invention.

Method 200 may start by stage 210 of placing an EUVL mask on a chuck and positioning a coupling module in a manner that allows multiple mask contact elements of the coupling module to contact the EUVL mask at multiple locations. The coupling module includes multiple coupling module conductive portions that are mutually isolated and are electrically coupled to the multiple mask contact elements.

The multiple coupling module conductive portions are electrically coupled to different elements of the chuck that are mutually isolated.

Stage 210 may be followed by stage 220 of evaluating whether a pair of coupling module conductive portions (of the multiple coupling module conductive portions) that should be shorted to each other via the EUVL mask are not shorted to each other. This may occur when the oxidation layer isolates the coupling module conductive portions of the pair. Alternatively, the coupling module conductive portions may be coupled to each other by a highly resistive path that may be formed by a partial formation of the oxidation layer.

If it is determined that all coupling module conductive portions that should be shorted to each other are shorted to each other, method 200 can end (as illustrated by END stage 260).

If it is determined that a pair of coupling module conductive portions that should be shorted to each other via the EUVL mask are not shorted to each other, then stage 220 should be followed by stage 230 of applying a voltage signal by the voltage supply between this pair of coupling module conductive portions.

Stage 230 may be followed by stage 240 of evaluating whether the pair of coupling module conductive portions that should be shorted to each other via the EUVL mask are not shorted to each other.

If it is determined that the pair of coupling module conductive portions that should be shorted to each other are shorted to each other, method 200 can end (as illustrated by END stage 260).

FIGS. 20-25 illustrate an EUVL mask and coupling modules according to various embodiments of the invention.

According to an embodiment of the invention, the EUVL mask can be supported by a mask holder—that has a mask cover 103 and a mask supporting element 101. The mask supporting module 101 can be regarded as being a part of the chuck or as being a part of the coupling module 20.

Figure 20:
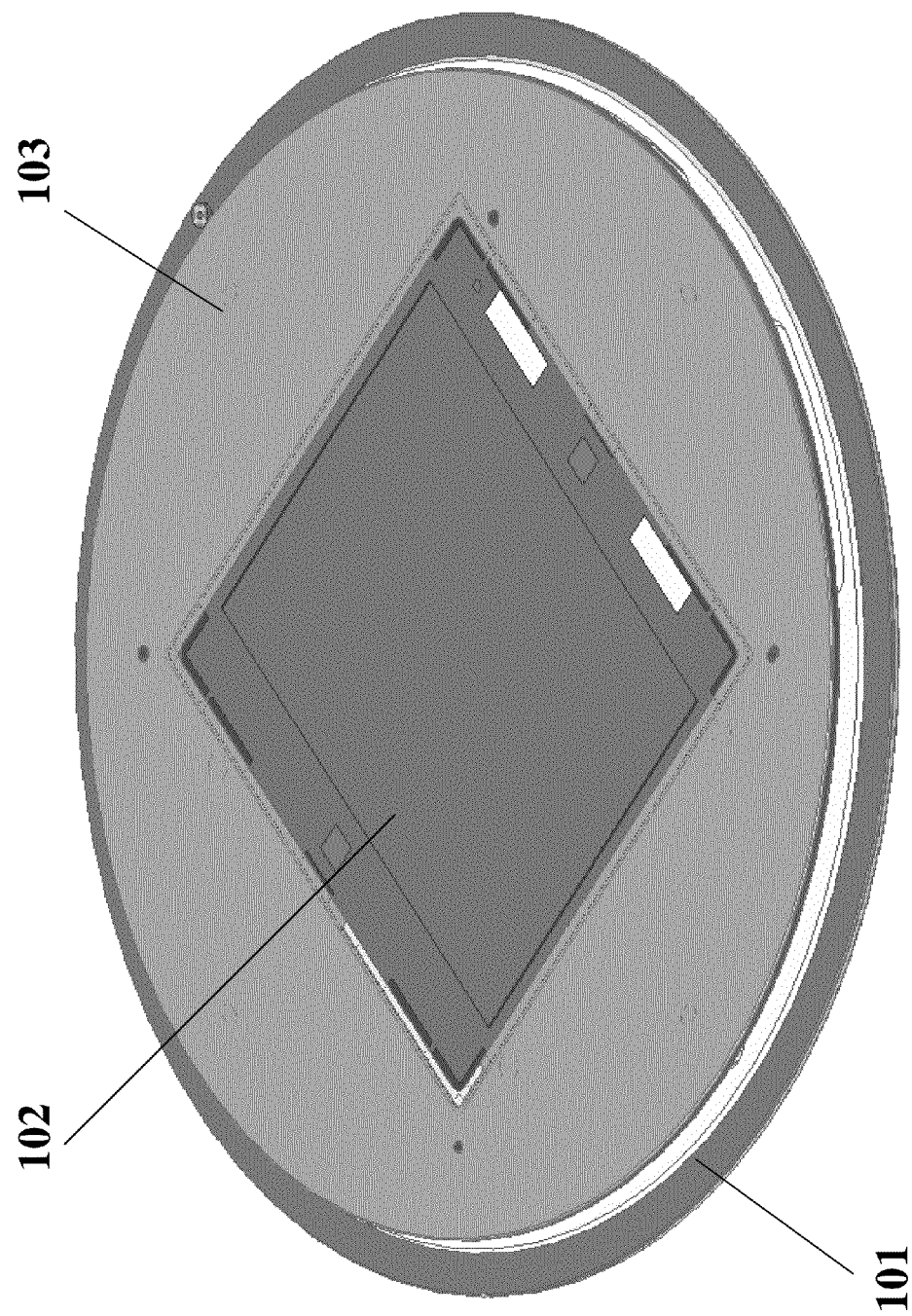
FIGS. 20-25 illustrate an EUVL mask and a coupling module, according to various embodiments of the invention.
Figure 21:
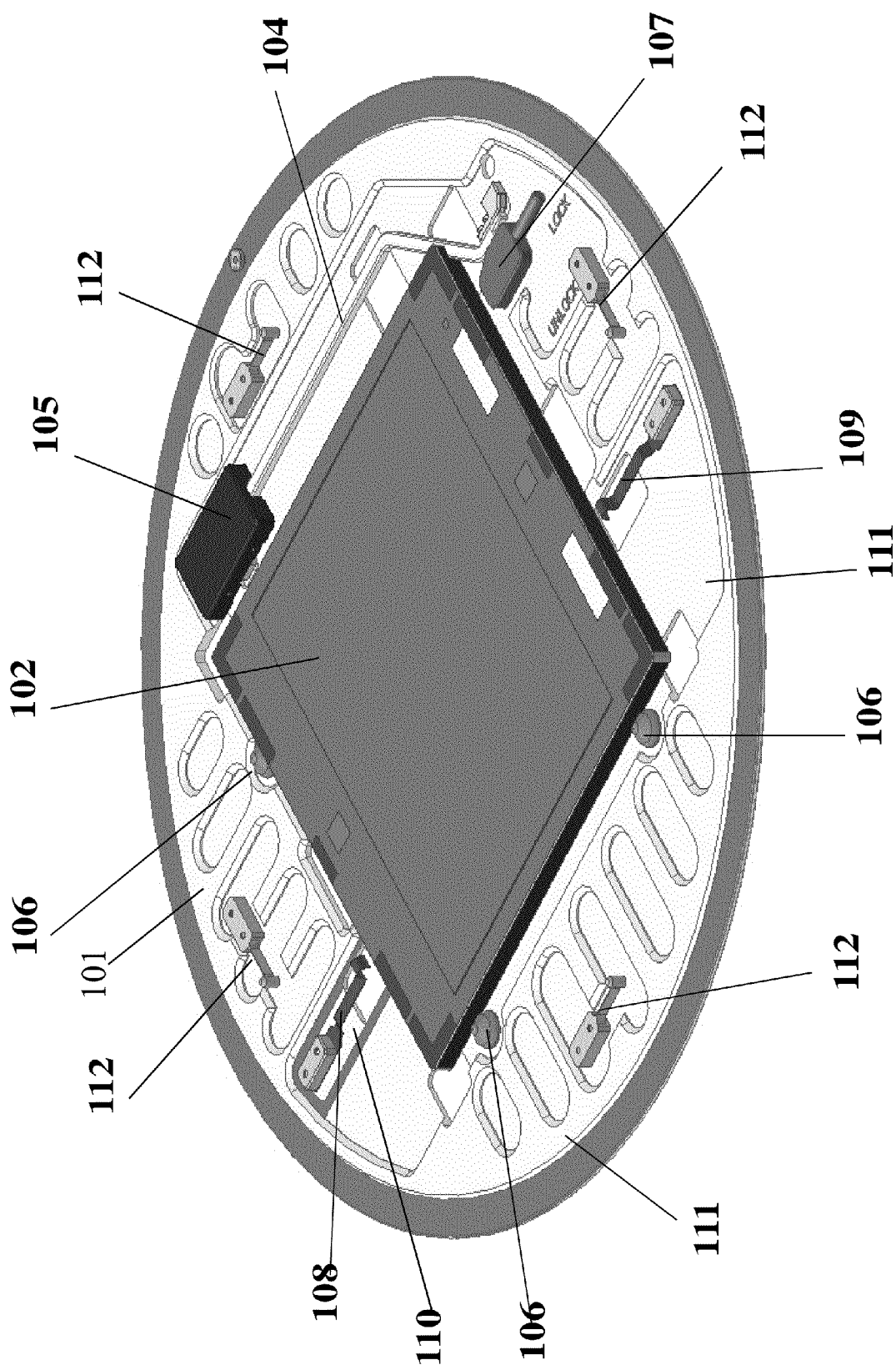
Figure 22:
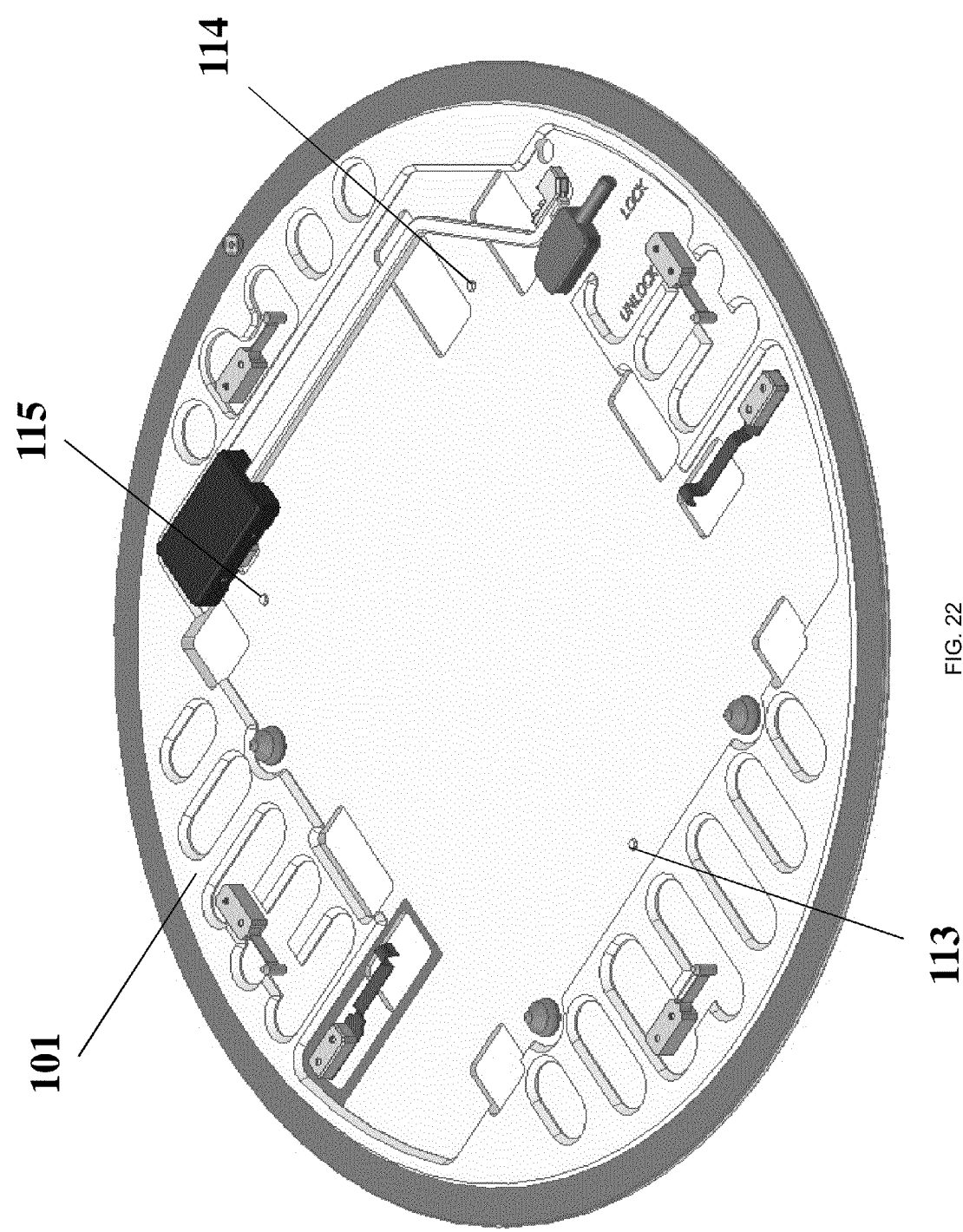
Figure 23:
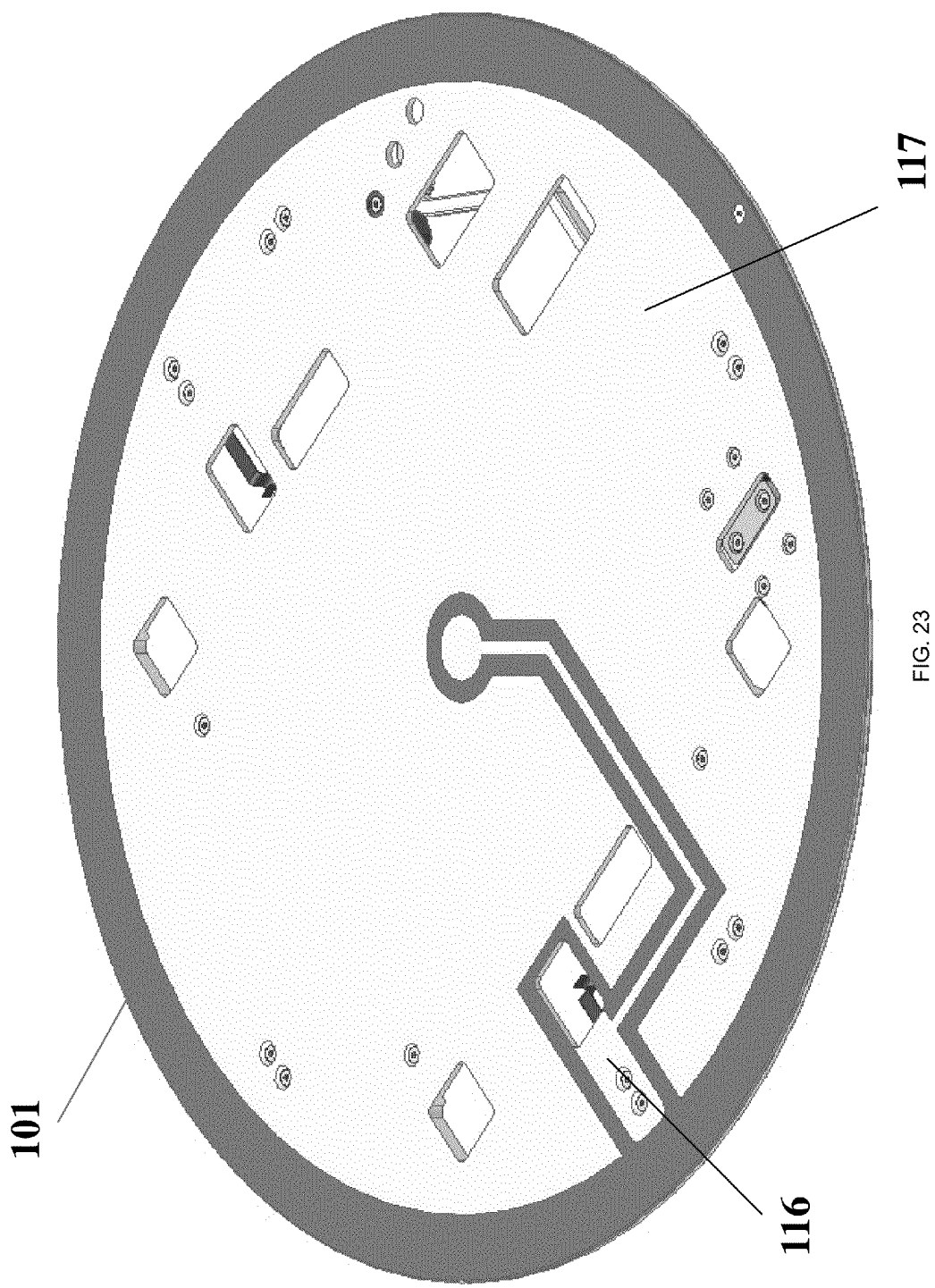
Figure 24:
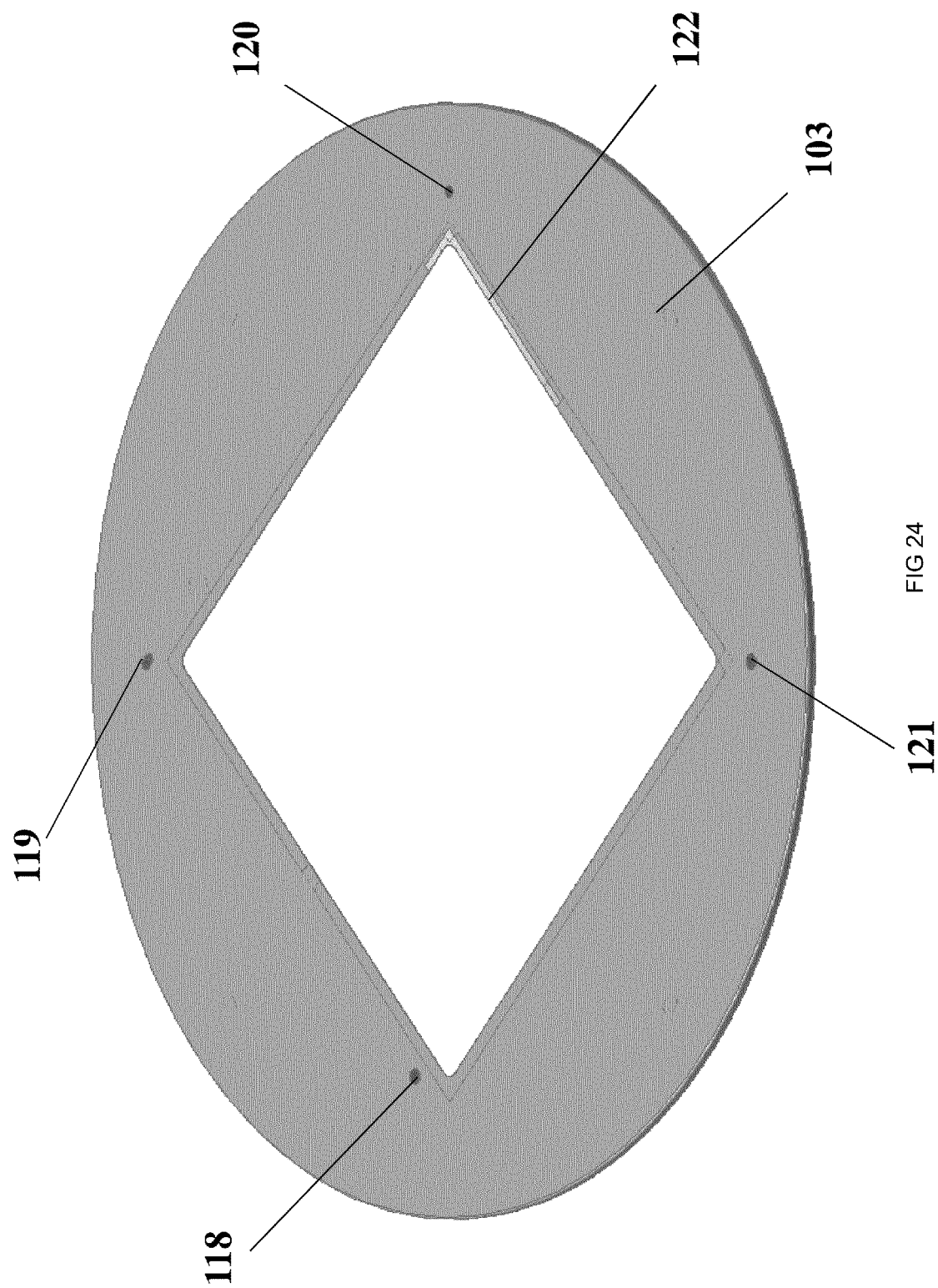
Figure 25:
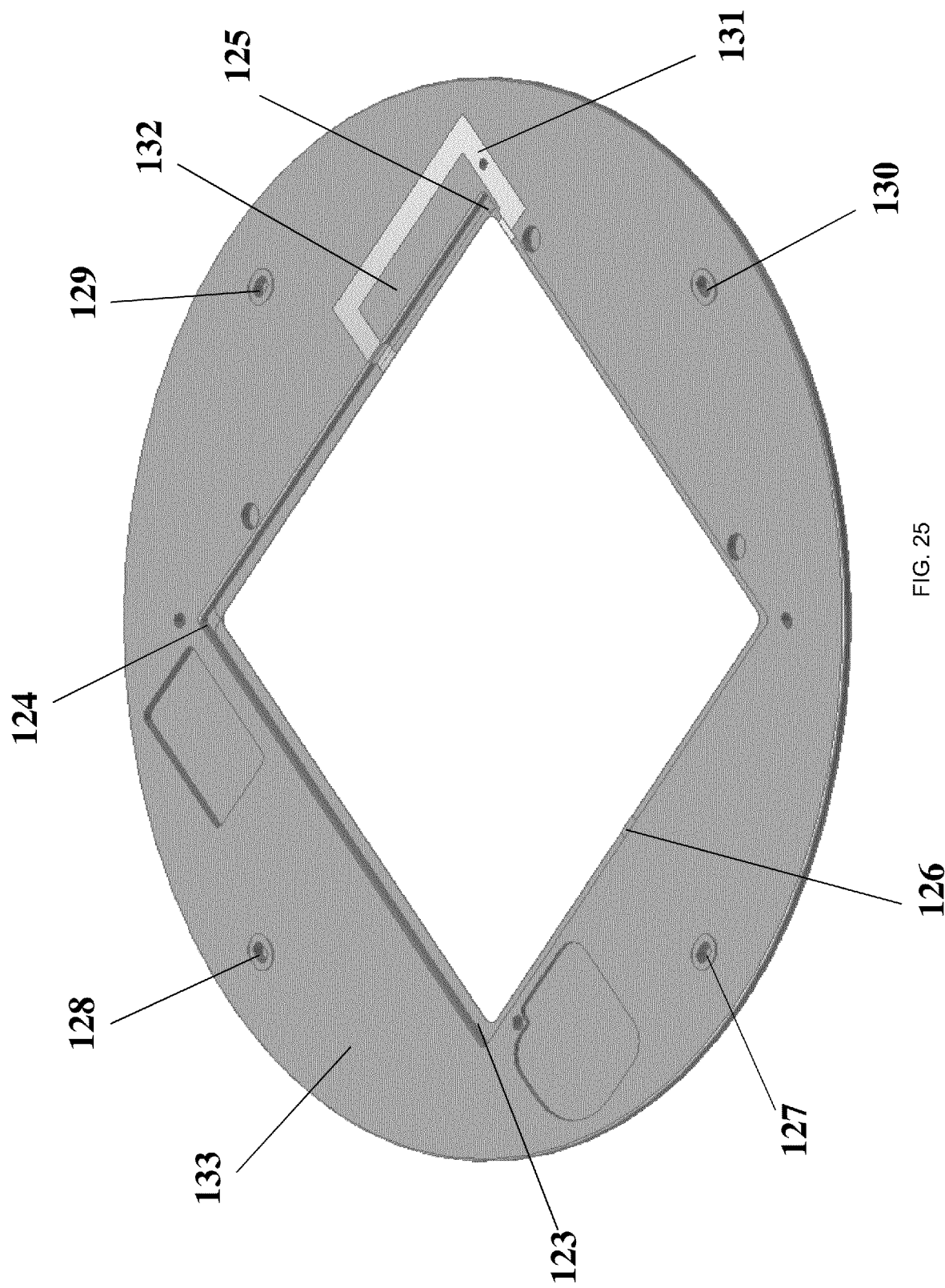

FIG. 20 provides an isometric view of a EUVL mask 102 and a coupling module that includes the mask cover 103 and the mask supporting module 101, according to an embodiment of the invention. FIG. 21 illustrates mask supporting module 101 and the EUVL mask 102 according to an embodiment of the invention. FIGS. 22 and 23 illustrate mask supporting module 101 according to various embodiment of the invention. FIGS. 24 and 25 illustrate a top view and a bottom view of mask cover 103 according to various embodiments of the invention.

Referring to FIG. 21, the mask supporting module 101 includes a mask aligning spring 104 with spring holder 105, three mask borders 106, aligning spring handle cam 107, two electrical contact springs 108 and 109, and four mask cover supports 112.

The mask supporting module 101 can be made of insulating ceramic, for example, Alumina with conductive coating, for instance, hard chrome. The front mask surface has two coating areas 110 and 111 that are separated by dielectric spaces. It allows connecting the contact springs 108 and 109 to different electrical potentials for an electrical conductivity test and an electrical zapping procedure. The aligning spring 104 may act on the EUVL mask's corner wedge, pushing the mask to engage with the three mask borders 106, thus carrying out mask alignment.

The hand cam 107 is designed for manual release of the EUVL mask 102 from the aligning spring 104. The automatic release is carried out by a special device (not shown). Four mask cover supports 112 are necessary to provide mask cover 103 with additional support that increases of the mask cover natural frequency.

FIG. 22 is an isometric view of the mask supporting module 101. A EUVL mask 102 can be located on the three bulges 113, 114 and 115 of the base holder 101. They are coated by a conductive coating, for example hard chrome, and contact with EUVL mask 102 via the mask area where mask contacts are allowed.

The back side of the holder base 101 is shown in FIG. 23, where the whole surface is divided into three areas. The first area is a large conductive coating area 117; the second area is the small conductive coating area 116 and the third area is an insulator area that separates the two conductive areas 116 and 117. The conductive area 116 is connected to the contact spring 108 and conductive spring 109 is connected to the conductive area 117. It is allows performing the electric conductivity test and zapping procedure.

FIG. 24 is an isometric view of the front side of the mask cover 103 and FIG. 25 provides an isometric view of the back side of mask cover 103, according to various embodiments of the invention.

Four holes 118, 119, 120 and 121 are intended for mount and dismount of the mask cover 103 on the front side of the EUVL mask 102. It is performed by a special mechanism (not shown). The cover 103 is made of an insulative material, for example Alumina ceramic, and has the conductive coating, for example hard chrome, on the whole surface except for surface 122 on the front side and surface 131 on the back side.

Referring to FIG. 25, this configuration of the conductive and insulating surfaces allows performing the electrical conductivity test and mask zapping procedure. On the back side surface of the mask cover 103, there are four slot pockets 127, 128, 129 and 130, which are intended for interaction with four mask cover supports 112 that increase the mask cover 103 natural frequency when it is mounted on the EUVL mask 102. The square pocket 126 on the central part of the mask cover 103 is intended for cover mounting on the EUVL mask 102. The mask cover 103 is contacted with EUVL mask 102 via three outstanding small surfaces 123, 124 and 125. From an electrical contact point of view, the outstanding surface 125 is the integral part of the surface 132 and two outstanding surfaces 123 and 124 are integral parts of the remaining coating part 133 of the back side of the mask cover 103. When the mask cover 103 is mounted on the EUVL mask 102 and EUVL mask 102 mounts on the mask base 111 (see FIG. 20), the contact spring 108 has an electrical contact with surface 132 and contact spring 109 has an electrical contact with surface 133. Such configuration allows performing the electrical conductivity test and mask zapping procedure. The orientation of the three outstanding surfaces 123, 124 and 125 depend on the orientation of the mechanical contacts' permitted areas on the front surface of the EUVL mask 102.

If it is determined that the pair of coupling module conductive portions that should be shorted to each other via the EUVL mask are not shorted to each (despite stage 230) then stage 240 may be followed by stage 230 or may be followed by stage 250 of changing the signal to be applied during stage 230. Stage 250 can be followed by stage 230. Stage 250 may include changing the signal (for example, increasing the voltage) to be supplied during the next iteration. Non-limiting values may range between a few volts through a few hundred volts, for example, between 3V and 400V.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A coupling module for coupling an extreme ultra violet (EUVL) mask to a chuck, the coupling module comprising:
   an upper portion that defines an aperture;
   at least one mask contact element;
   chuck contact elements; and
   an intermediate element connected between the mask contact elements and the upper portion;
   wherein a shape and a size of the aperture corresponds to a shape and size of a pattern transfer area of the EUVL mask;
   wherein the coupling module is shaped and sized so that once the at least one mask contact element contacts an upper portion of the EUVL mask, the chuck contact elements contact a chuck that supports the EUVL mask; and
   wherein the coupling module provides at least one conductive path between the upper portion of the EUVL mask and the chuck, when the EUVL mask is positioned on the chuck in alignment with the coupling module.

2. The coupling module according to claim 1, wherein when the EUVL mask is positioned on the chuck, the coupling module masks edges of the EUVL mask.

3. The coupling module according to claim 1, wherein at least one mask contact element comprises a spring.

4. The coupling module according to claim 1, wherein a height difference between the upper portion and a bottom end of the intermediate element is smaller than a height of the EUVL mask.

5. The coupling module according to claim 1, wherein the mask contact elements are positioned so as to contact the EUVL mask at locations that are outside the pattern transfer area.

6. The coupling module according to claim 1, wherein the aperture exposes the pattern transfer area once the coupling module is placed on the EUVL mask.

7. The coupling module according to claim 1, wherein the intermediate element is shaped so as to surround the EUVL mask.

8. The coupling module according to claim 1, wherein the intermediate element is shaped so as to contact at least one sidewall of the EUVL mask, when the coupling module is placed on the EUVL mask.

9. The coupling module according to claim 1, wherein the coupling module is symmetrical about a center of the EUVL mask.

10. The coupling module according to claim 1, wherein the coupling module is made of stainless steel.

11. The coupling module according to claim 1, wherein the at least one conductive path is formed by a conductive coating of a non-conductive coupling module.

12. The coupling module according to claim 1, wherein the at least one conductive path comprises multiple conductive paths.

13. The coupling module according to claim 1, wherein at least one mask contact element is arranged to loosely contact the chuck when the coupling module is placed on the EUVL mask.

14. The coupling module according to claim 1, wherein the coupling module comprises multiple coupling module conductive portions that are isolated from each other; wherein different coupling module conductive portions are coupled to different mask contact elements; and wherein each mask contact element electrically couples a coupling module conductive portion to the EUVL mask.

15. A method for inspecting an extreme ultra violet (EUVL) mask, the method comprising:
   placing on a chuck an EUVL mask and a coupling module, wherein the coupling module electrically couples an upper portion of the EUVL mask and the chuck; and
   scanning at least a portion of a pattern transfer area of the EUVL mask by a charged particle beam that passes through an aperture defined by an upper portion of the coupling module, while the chuck, the coupling module and the charged particle beam are located in a vacuum chamber.

* * * * *